(12) United States Patent
Lagin

(10) Patent No.: US 6,180,092 B1
(45) Date of Patent: Jan. 30, 2001

(54) DISSOLVABLE AIR FRESHENER

(76) Inventor: Arlene Lagin, 7401 N. Scottsdale Rd., #49, Scottsdale, AZ (US) 85253

(*) Notice: Under 35 U.S.C. 154(b), the term of this patent shall be extended for 0 days.

(21) Appl. No.: 08/337,169

(22) Filed: Nov. 10, 1994

(51) Int. Cl.[7] .................................................. A61L 9/04
(52) U.S. Cl. ........................... 424/76.4; 424/76.21; 512/4
(58) Field of Search ............................... 424/76.4, 76.21, 424/466; 512/4

(56) References Cited

U.S. PATENT DOCUMENTS

| | | | | |
|---|---|---|---|---|
| 3,261,746 | * | 7/1966 | Capley | 512/4 |
| 3,446,893 | * | 5/1969 | Hanford et al. | 424/76.4 |
| 5,041,421 | * | 8/1991 | King | 512/4 |
| 5,198,144 | * | 3/1993 | Ichii et al. | 252/174.11 |

OTHER PUBLICATIONS

Kruse et al, Chem Abst., vol. 118, #240, 491 (1993).*
Krause et al, Chem. Abst., vol. 119, #98507 (1993).*
Hirata et al., Chem., Abst, vol. 119, #15044 (1993).*
Ichii et al, Chem. Abst. vol, 113, #11938q (1990).*

* cited by examiner

Primary Examiner—James H. Reamer
(74) Attorney, Agent, or Firm—Snell & Wilmer, L.L.P.

(57) ABSTRACT

The present invention relates to a granular air freshener capable of being dissolved in water. It is comprised of a chemical carrier and a selected scent incorporated together. The chemical carrier is one which effervesces when dissolving or dissolved in water. As the carrier dissolves, the gas emitted (e.g., carbon dioxide) as it effervesces carries with it the selected scent to freshen the air in the room in which the freshener is dissolved. The invention is ideal for single use packaging for traveling and public use.

8 Claims, No Drawings

DISSOLVABLE AIR FRESHENER

FIELD OF THE INVENTION

The present invention relates to an air deodorizer that is soluble in water. More particularly, the invention relates to a combination of a perfume and a chemical matrix carrier that, when deposited in water (such as in a toilet bowl), effervesces and dissolves and releases a harmless gas that carries with it the perfume scent to freshen the air in a room.

BACKGROUND OF THE INVENTION

The voluminous selection of available room fresheners attests to the great need for air deodorizers in today's society. There are several styles of air fresheners available on the market today—from aerosol sprays, to solid type fresheners, to ones that are plugged into an outlet (known as PLUG-INS). Additionally, as is evident to everyone, the room in which there is the greatest need for any type of air freshener or room deodorizer is in the bathroom. Unfortunately, the types of air fresheners on the market today are not conducive to carrying in one's pocket or purse. This often leads to uncomfortable or embarrassing situations when one uses a public or guest's bathroom and is without an air freshener.

The present invention addresses this problem by providing a chemical air freshener that is dissolvable in water, and may be packaged in a small single-use amount. The air freshener is comprised of a chemical matrix carrier, combined with a selected perfume scent. The chemical matrix carrier is one that will effervesce when placed in water, and will release a gas (usually carbon dioxide). As the carbon dioxide gas evolves and raises from the water in which the freshener is dissolving, it carries with it the selected perfume scent incorporated within the carrier. This way, one can use the toilet at a public place or at a guest's house, and throw an amount of air freshener of the present invention into the toilet to dissolve in the toilet water and freshen the air in the bathroom.

Accordingly, it is an object of the present invention to provide an air freshener comprised of a combination of perfume and chemical carrier capable of dissolving in water and emitting the scent of the perfume used.

It is a further object of the present invention to provide an air freshener in a powdered form, packaged in a single-use amount, said air freshener dissolvable in water to emit a given scent.

The present invention, additionally, provides a suitable and functional powder which can be compressed in a tablet form in various shapes and sizes. Both single-use powder and single-use tablets are contemplated in this invention.

SUMMARY OF THE INVENTION

In accordance with these and other objects of the present invention, an air freshener is provided comprised of a chemical matrix carrier that is dissolvable in water. Incorporated into this chemical carrier is a given scent or perfume that is dissipated into the air as said chemical carrier dissolves in water.

DETAILED DESCRIPTION OF THE INVENTION

For the practice of one embodiment of the present invention, one must first create a suitable chemical matrix carrier capable of dissolving in water, and which effervesces to release a gas when dissolving. Such a carrier may be comprised of citric acid and/or adipic acid and sodium bicarbonate. This combination creates a water soluble matrix which effervesces when dissolving, and releases carbon dioxide gas.

The citric acid and/or adipic acid used is the anhydrous grade (citric acid is available from Miles Laboratories, Elkhart, Ind.; adipic acid is available from DuPont, Wilmington, Del. or Monsanto, St. Louis, Mo.). Additionally, the anhydrous form of sodium bicarbonate is also used (available from Arm & Hammer, or Mallinkrodt, St. Louis, Mo.). It is important to use the anhydrous form to eliminate any water content in the chemical matrix carrier as moisture and water content can trigger the effervescence reaction prematurely.

Incorporated into the chemical matrix carrier is a mixture of silicon dioxide and perfume oil. The present invention utilizes a powder composition air freshener, which exhibits affinity for moisture absorption. Excess moisture absorption may cause caking of the powder. Therefore, the powder mixture must contain an anti-caking agent, in this case, silicon dioxide. A form of silicon dioxide called SIPERNAT, available from Degussa, Germany, may be used in one embodiment of the invention. Other anti-caking agents known in the art, such as aluminates and silicates, may also be used.

Any perfume oil known in the art may be used in the present invention, including those oils available from specialty perfume houses such as IFF (International Flavor and Fragrance, New Jersey); Ungerer, Elias Fragrances (New Jersey); Haarmann & Reimer (New Jersey); or Roure-Guvidan (New Jersey). Scents such as vanilla (vanillin), almond/cherry (benzaldehyde), baby powder, and other designer types may be used. Designer type perfume or cologne known in the art may also be used.

For the manufacture of an air freshener of the present invention, all equipment and utensils must be thoroughly dried. In a first completely dry vessel, add a pre-weighed amount of citric acid and/or adipic acid and sodium bicarbonate. Mix these two ingredients thoroughly. In a second completely dry vessel, combine an amount of silicon dioxide and perfume oil. Mix the silicon dioxide and perfume oil until a flowable perfume powder concentrate is formed. This perfume powder concentrate is then added to the first vessel containing the citric acid and/or adipic acid, and sodium bicarbonate. The ingredients are thoroughly mixed. After sufficient mixing of the finished composition, the air freshener is ready for packaging. Dusting throughout the entire process must be prevented.

The final product should be packaged and sealed in air tight, water resistant packages. For example, plastic jars or bags, or foil coated bags, may be used for packaging. Additionally, the final powder may be compressed into tablets. In order to compress the final product into tablets, adjustments known in the art must be made to the chemical matrix carrier.

One-half ounce of the final powder is enough for one use of the air freshener of the present invention. This amount of perfume powder is placed in the water in a toilet bowl, the citric and/or adipic acid and sodium bicarbonate react to effervesce and release carbon dioxide gas. The carbon dioxide gas, as it evolves from the water, carries with it the dissolved perfume scent, freshening the air in the bathroom.

The weight percentage of powdered ingredients used in making the air freshener of the present invention is approximately as follows: citric and/or adipic acid between around 15% and 30%; sodium bicarbonate and/or sodium carbonate between around 60% and 80%; and silicon dioxide between around 5% and 10%. The amount of perfume oil used may vary, depending on the strength desired.

The following example, created as described above, depicts one available embodiment of an air freshener of the present invention:

EXAMPLE 1

To create 100 pounds of peppermint scented room deodorizer, in a completely dry first vessel combine 40 pounds of citric acid anhydrous (Miles Laboratories) and 32 pounds of sodium bicarbonate anhydrous (Mallinkrodt). Mix thoroughly. In a second completely dry vessel, combine 25 pounds of peppermint fragrance #15078 from Elias Fragrances Inc., New York, N.Y., and 3 pounds of SIPERNAT 22. Mix the peppermint fragrance and SIPERNAT until the fragrance oil is completely absorbed into the SIPERNAT, forming a dry flowable powder.

Add the perfume/SIPERNAT combination to the first vessel, mixing thoroughly to combine all ingredients. The freshener in then ready for packaging and use.

EXAMPLE 2

To prepare 100 pounds of vanilla scented air deodorizer, place 15 pounds of SIPERNAT in a dry kettle. Add 8 pounds of vanilla fragrance and mix until a dry flowable powder fragrance concentrate is obtained. To this kettle, add 47 pounds of sodium bicarbonate, 10 pounds of sodium carbonate, 15 pounds of citric acid and 5 pounds of adipic acid. Tumble entire mixture until uniform. The blend is then ready for packaging.

A benefit of the air freshener of the present invention is that the perfume powder may be packaged in single use packages, which may be carried in one's purse or pocket. When using a public bathroom or a friend's bathroom, one may then open a package of the air freshener of the present invention and dispense the contents into the water in the toilet. This would then release the scent used in the composition and freshen the air in the bathroom.

The invention has been described in detail with particular reference to a preferred embodiment thereof, but it will be understood that the invention is capable of other and different embodiments. As is readily apparent to those skilled in the art, variations and modifications can be affected within the spirit and scope of the invention. Accordingly, the foregoing disclosure, description are for illustrative purposes only, and do not in any way limit the invention, which is defined only by the claims.

I claim:

1. A granulated air freshener, said granulated air freshener comprised of:
   a chemical matrix carrier capable of dissolving in water comprising between about 15% and about 30% of citric acid and/or adipic acid and between about 60% and about 80% of sodium bicarbonate and/or sodium carbonate;
   a selected scent; and
   an anti-caking agent to prevent caking or clumping of said granulated air freshener.

2. The air freshener of claim 1 wherein said selected scent is comprised of a perfume oil.

3. The air freshener of claim 1 wherein said anti-caking agent is comprised of silicon dioxide.

4. An air freshener capable of dissolving in water and releasing a desired scent, said air freshener comprised of
   between about 15% and about 30% of citric acid and/or adipic acid;
   between about 60% and about 80% of sodium bicarbonate and/or sodium carbonate;
   between about 5% and about 10% silicon dioxide; and
   up to about 20% perfume oil.

5. The air freshener of claim 4 wherein said perfume oil is selected from the group consisting of vanillin, benzaldehyde, baby powder scent, peppermint oil, spearmint oil, wintergreen oil, and a designer cologne oil.

6. A method of making a granular air freshener capable of dissolving in water, said method comprised of
   thoroughly drying a selected first vessel to remove all water and moisture therein;
   combining a selected amount of citric acid and/or adipic acid, and sodium bicarbonate and/or sodium carbonate in said dried first vessel;
   thoroughly drying a selected second vessel to remove all water and moisture therein;
   combining a selected amount of anti-caking agent and perfume oil in said dried second vessel;
   mixing the contents of said second vessel with the contents of said first vessel thereby forming said granular air freshener.

7. The method of claim 6 wherein said anti-caking agent is comprised of silicon dioxide.

8. The method of claim 6 wherein said perfume oil is selected from the group consisting of vanillin, benzaldehyde, baby powder scent, peppermint oil, spearmint oil, wintergreen oil, and a designer cologne oil.

* * * * *